United States Patent [19]

Solomon et al.

[11] Patent Number: 5,334,390

[45] Date of Patent: Aug. 2, 1994

[54] METHOD FOR TABACCO DEHABITUATION

[76] Inventors: Neil Solomon, 2209 Ken Oak Rd., Baltimore, Md. 21209; Theodore C. Solomon, 3006 Benson Mill Rd., Upperco, Md. 21155; Allen J. Freed, 47-40 Glenwood St., Little Neck, N.Y. 11362

[21] Appl. No.: 971,539

[22] Filed: Nov. 5, 1992

[51] Int. Cl.[5] .................... A61K 9/14; A61K 47/36
[52] U.S. Cl. ............................ 424/439; 424/489; 424/500; 424/687; 514/782
[58] Field of Search ............... 424/440, 439, 489, 500, 424/686, 687; 514/782

[56] References Cited

U.S. PATENT DOCUMENTS 2,705,695  4/1955  Rapp ........................... 167/65
4,778,677 10/1988  Ebbesen ....................... 424/128
4,980,172 12/1990  Fey ............................ 424/485

OTHER PUBLICATIONS

Schachter, Stanley, "Nicotine Regulation in Heavy and Light Smokers", *Journal of Experimental Psychology: General*, 1977 vol. 106, No. 1, pp. 5–12.

Schachter et al, "Studies of the Interaction of Psychological and Pharmacological Determinants of Smoking", *Journal of Exp. Psy: General*, 1977, vol. 106, No. 1, pp. 3–4.

Silverstein et al, "Social Life, Cigarette Smoking, and Urinary pH", *Journal of Exp. Psy: General*, 1977, vol. 106, No. 1, pp. 20–23.

Schachter et al, "Effects of Urinary pH on Cigarette Smoking", *Journal of Exp. Psy: General*, 1977, vol. 106, No. 1, pp. 13–19.

Schachter et al, "Psychological and Pharmacological Explanations of Smoking Under Stress", *J. of Exp. Psy: General*, 1977, vol. 106, No. 1, pp. 31–40.

Dr. Neil Solomon, *Stop Smoking Lose Weight*, Kensington Publishing Corp., New York, New York, 1981.

*Primary Examiner*—Edward Webman
*Attorney, Agent, or Firm*—Hoffman, Wasson & Gitler

[57] ABSTRACT

Method for alleviating symptoms of nicotine withdrawal employing calcium carbonate.

23 Claims, 1 Drawing Sheet

/ 1

METHOD FOR TABACCO DEHABITUATION

BACKGROUND OF THE INVENTION

The invention relates to a method for alleviating symptoms of tobacco withdrawal in humans dehabituating from a tobacco habit over a withdrawal period of several weeks. In particular, the invention relates to a regimen for dehabituating humans from the use of tobacco, particularly smoking, with decreased recidivism rates.

The use of tobacco has been characterized as one of the most difficult of habits to break. Many methods have been proposed for assisting tobacco users in their efforts to permanently reduce or eliminate their dependency on tobacco, most of which are directed to the modification of their behavior or physiology to alleviate withdrawal symptoms of nicotine (the generally acknowledged active factor in this habit, see e.g., *J. Exp. Psy. General* 106, p. 5, No. 1, 1977, Schachter, Silverstein, et al.: "Because cigarette smoking can be a difficult habit to correct, it is generally assumed that tobacco is addictive with nicotine as the active agent."), and thereby curb the customary urge to resume the use of tobacco. The physiological effects of nicotine on the human body are complex, however, and it has proved difficult to correlate physical and psychological withdrawal symptoms with these effects and provide a simple, efficacious, and non-toxic pharmaceutical treatment which alleviates these symptoms. As a result, few of these methods have proved consistently effective, and recidivism is common, even when an extended period of abstention has been achieved.

DISCUSSION OF RELATED ART

Typical known pharmaceutical treatments include tobacco substitutes such as nicotine chewing gum or lobeline sulfate (see, e.g., U.S. Pat. No. 2,705,695 to Rapp); deterrents such as astringent mouthwashes which irritate the oral and nasal mucosa; and tranquilizers or other relaxants to reduce psychological symptoms such as tension and irritability. More sophisticated treatments are directed to the correction of physiological disorders believed to be at least in part responsible for tobacco withdrawal symptoms; U.S. Pat. No. 4,778,677 to Ebbssen, for example, describes the use of a composition comprising glucose, potassium ions, and caffeine to alleviate symptoms of nicotine withdrawal including tremors, anxiety, nervousness, craving and irritability, based on the theory that nicotine withdrawal induces hypokalemia and hypoglycemia which are responsible for these symptoms.

More recently, a series of articles in the Journal of Experimental Psychology (*J. Exp. Psy. op, cit., pp.* 3-4, 13-19, and 20-40) has attempted to correlate urine pH with the desire for nicotine in smokers. The authors provide data supporting their hypothesis that 1) urine pH has a significant effect on excretion of unmetabolized nicotine and 2) that confirmed smokers tend to closely regulate nicotine levels in their bodies; the authors theorize on the basis of their data that individuals who have near-optimal levels of nicotine in their blood plasma and who are attempting to maintain these optimal levels increase their smoking rate as urine acidification increases, as is common, for example, in stress situations. This art suggests that under such circumstances, the excretion rate of unmetabolized nicotine increases as urine acidity increases, and that smokers compensate for this loss by increasing nicotine intake, according to customary principles of biofeedback mechanisms. This art further suggests that this phenomenon can be counteracted by administration of sodium bicarbonate in amounts sufficient to effect neutralization or alkalinization or the urine and decreased loss of nicotine; the intake of nicotine necessary to maintain existing levels is then concomitantly reduced. As a result, fewer cigarettes must then be consumed to maintain individual desired nicotine levels and the smoking rate does not increase (*J. Exp. Psy. op. cit., pp.* 38–39). The authors also emphasize that their data is consistent with a theory that heavy smoking results in acidification of the urine (*J. Exp. Psy. op. cit., p.* 19).

This concept of reducing urine acidity to neutral or alkaline levels to reduce the rate of nicotine elimination from the system and to therefore reduce nicotine withdrawal symptoms has been applied as described in *Stop Smoking, Lose Weight* (Solomon, Neil; Zebra Press, Kensington Publishing Corp., 475 Park Ave. South, New York, N.Y., 1986), wherein sodium bicarbonate at individually determined levels was reported as having been prescribed to prevent a precipitous decline in nicotine levels on withdrawal and a concomitant sharp and most often irresistible increase in nicotine craving in patients who were attempting to stop smoking (pp. 86, 87); alternatively, dietary alkalinizing sources such as vegetables were used to increase system alkalinity (pp. 124, 125). It has been found, however, that sodium bicarbonate in the amounts necessary to effect adequate urine alkalinization has unpleasant side effects such as flatulence, diarrhea, and nausea; furthermore, the use of sodium in such amounts is contraindicated in patients having diseases or disorders requiring a low sodium intake, notably hypertension.

While the art suggests that an amount of sodium bicarbonate in oral dosages sufficient to obtain a neutral or alkaline urine has the effect of delaying excretion of unmetabolized nicotine from the body if the urine is otherwise acid and if an about optimal nicotine level is otherwise present, with a concomitant delay of withdrawal symptoms, there has been no suggestion that alkalinizing agents as a group or sodium bicarbonate (used in the Schachter and Solomon studies) in particular might mitigate nicotine withdrawal symptoms over a significant period of time and thus might be consequently useful as agents to break the habit of tobacco use. To the contrary, in *J. Exp. Psy. op. cit., p.* 35, it is stated that plasma nicotine levels after a night's sleep are at or close to zero, and that any change in urine pH at this stage has a trivial effect on smoking rates. The above-noted art is clear that it has been believed that it is only when the system has its full or nearly full complement of nicotine that administration of sodium bicarbonate to increase urine pH under otherwise acid conditions is a factor in smoking rate and that any use of sodium bicarbonate to break a tobacco habit is highly fugitive, with effects that may last at best for a day or so. Any effect of an alkalinizing agent in an amount sufficient to neutralize or alkalinize acid urine to reduce nicotine withdrawal symptoms or craving for tobacco over a prolonged withdrawal period of customarily several weeks is therefore entirely unexpected.

SUMMARY OF THE INVENTION

The invention comprises a method for alleviating symptoms of nicotine withdrawal in humans habituated to tobacco, consisting essentially of administering calcium carbonate to a human habituated to tobacco in an amount sufficient to maintain the urine of the human at a neutral to alkaline pH. The alkalinizing agent is easily administered orally, has few or no side effects such as flatulence, diarrhea, or nausea at effective dosages, effectively controls nicotine craving and minimizes withdrawal symptoms, is easily combined with a dietary regimen to potentiate alkalinization and further reduce nicotine withdrawal symptoms, and minimizes characteristic weight gain during the withdrawal period; the cation (calcium) is not contraindicated for patients with, for example, hypertension, and on the contrary is beneficial for various disorders such as osteoporosis.

The invention further includes a method for dehabituating humans to the use of tobacco, comprising administering calcium carbonate in an amount sufficient to maintain the urine at a pH of at least about 7. Preferably, the method further includes dietary and behavioral modifications which reinforce dehabituation, and comprises, for example, administration of an alkalinizing composition consisting essentially of calcium carbonate and gum karaya in amounts sufficient to maintain the urine at a pH of at least about 7.

BRIEF DESCRIPTION OF THE DRAWING

The sole FIGURE illustrates the total number of patients in each group reporting complete abstinence from smoking from the beginning of the study described in Example II to each data (time) point, on a percentage basis.

DETAILED DESCRIPTION OF THE INVENTION

Figure 1:
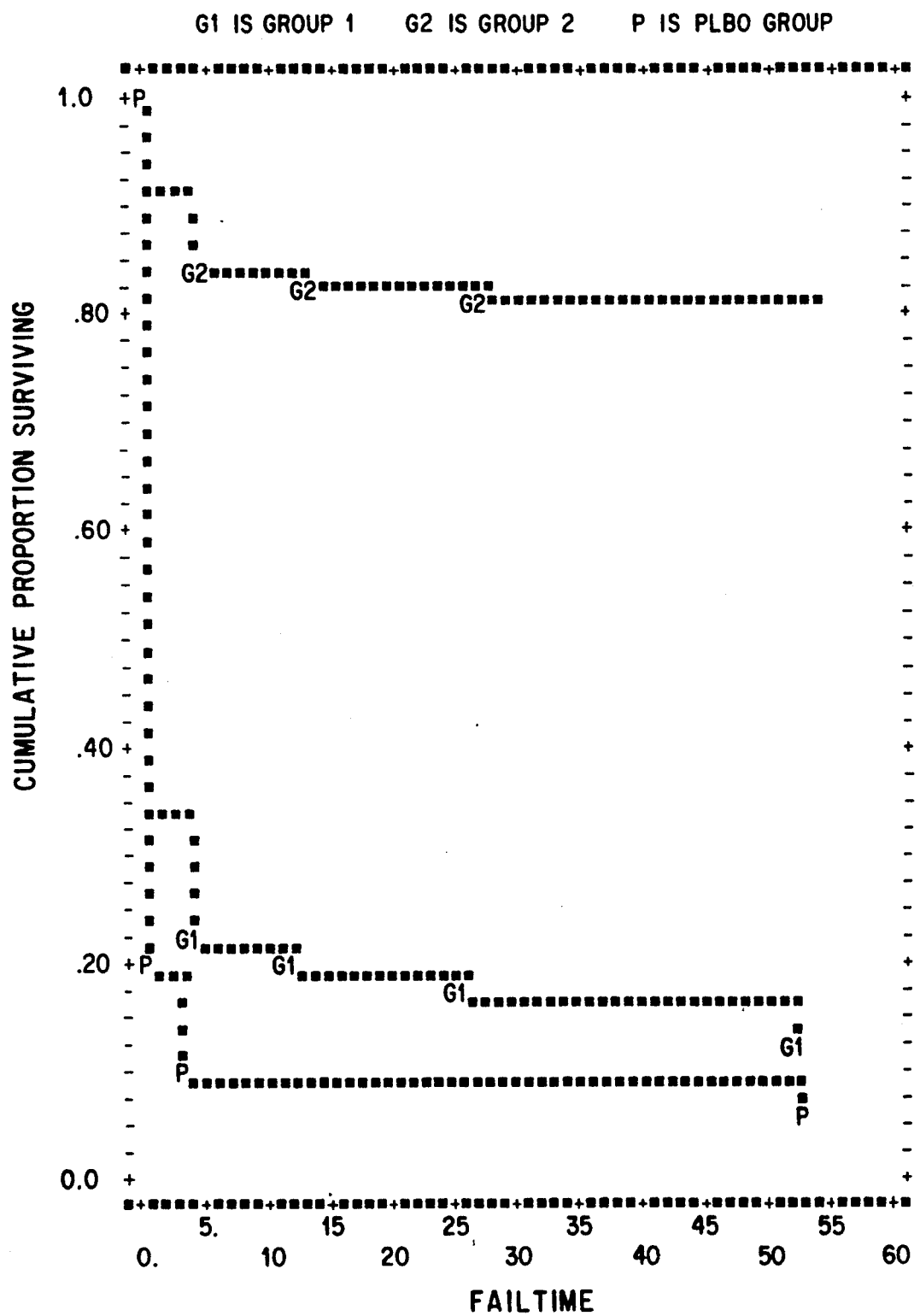

According to the invention, calcium carbonate in an amount sufficient to maintain urine pH at least about 7 is administered orally to a human attempting to break an habituation to tobacco, particularly the smoking of cigarettes. Preferably, the calcium carbonate is administered as a composition comprising calcium carbonate and gum karaya in an amount of from about one part gum karaya to 18 parts calcium carbonate, to reduce nicotine withdrawal symptoms and further to reduce appetite to preclude substantial weight gain attributable to a decrease in nicotine ingestion. The ingredients are suitably compounded in powder form, and ingested as a drink, wherein the powdered ingredients are dissolved in any convenient liquid. Exemplary dosages for a human weighing from about 90 to about 250 pounds include from about 2 to 10 grams calcium carbonate per day for the duration of a withdrawal period of about four weeks. Preferably, larger dosages within this range are administered during week one, for example, about 6 to 10 grams calcium carbonate, and the dosage is reduced for the remainder of the withdrawal period to, for example, from about 2 to 6 grams calcium carbonate per day, all preferably in substantially equal divided dosages of about at least two or more times per day. To reduce nicotine craving and minimize weight gain during the withdrawal period, the regimen further preferably comprises a diet reduced in calories in the amount of from about 15 to at least 25 calories per cigarette habitually smoked per day, urine alkalinization to maintain a urine pH of at least about 7, and sufficient exercise to release beta-endorphins in an amount at least equivalent to the beta-endorphins released by the ingestion of tobacco in the habitual amount; daily exercise burning at least about 15 calories per cigarette, preferably up to about 25 calories, habitually smoked per day is representative of suitable beta-endorphin production. In order to minimize weight gain during the withdrawal period and after, a dietary regimen during the withdrawal period of from about 1500 to about 2500 calories per day, depending upon the weight of the subject, as known in the art, is suggested.

EXAMPLES

Methods and Materials

Urine pH was measured with CHEMSTRIP (Boehringer Mannheim, Indianapolis, Ind., U.S.).

In Example I, variables coded "Success" ("S") indicate that all variables are "S" i e no failures were recorded in the patient history; variables coded "Failure" ("F") indicate that at least one value is "F" i e that at least one failure (return to smoking) was recorded in the patient history; patients were never returned to "S" after a failure ("F") was recorded.

In Example II, statistical analysis was performed using a two factor (treatment and time) repeated measures design, wherein measurements were made of the same variable (smoking satiation) for each subject at different times, unless otherwise indicated. Owing to the imbalance in packs of cigarettes per day smoked by the patients studied, analysis of covariance was used.

Control and experimental groups were chosen at random from a collective patient group habituated to tobacco (typically cigarette smoking) and desiring to dehabituate by their testimony. At least 30 patients were in each group. All patients received substantially the same instructions regarding diet and exercise in conjunction with treatment.

Group 1 (control group) received orally 8 grams sodium bicarbonate per day during week 1, and 4 grams sodium bicarbonate per day for the second, third and fourth weeks; Group 2 (experimental group) received orally 8 grams of calcium carbonate and 0.43 grams of gum karaya per day during week 1, and 4 grams of calcium carbonate per day (no gum karaya) during weeks 2, 3 and 4. Group 3 (placebo group: PLBO) received orally 22 grams of placebo during week 1, and 11 grams of placebo per day for the second, third and fourth weeks. Each patient received the daily alkalinizing agent or placebo dose in substantially equal divided dosages three times per day, dissolved in a liquid of their choice. Urine pH was tested at each patient visit to confirm that alkalinity (pH $\geq$ 7) was maintained in Groups 1 and 2.

Sodium bicarbonate powder was obtained from Church and Dwight Company, Princeton, N.J., U.S.

Calcium carbonate powder was obtained from United State Gypsum Corporation, Chicago, Ill., U.S.

Placebo powder was obtained from Foodworks, Inc., Flushing, N.Y., U.S.

Sources

BMDP Statistical Software, WJ Dixon, Editor, University of California Press, Berkeley, 1988.

Program 2V: Analysis of Variance and Covariance, Including Repeated Measures, pp. 483–519

Program 7D: One- and Two-Way Analysis of Variance with Data Screening, pp. 187–209 Includes several pairwise multiple comparison tests (Bonferroni and Dunnett were used)

Program 1L: Life Tables and Survival Functions

*Statistical Principles in Experimental Design,* BJ Winer, McGraw-Hill Book Company, New York, 1962, pp. 298-312.

Definitions

"Smoking satiation" is defined herein as the desire to smoke, on a scale of 1 to 10. Number ten (10) was self-assigned if the subject, based on previous experience, had no desire to smoke. Number zero (0) was self-assigned if the subject had the same desire to smoke as previously experienced.

"Maximum smoking satiation" was achieved when the patient was calm and peaceful and not experiencing agitation, in contrast to the non-satiated group.

EXAMPLE I

|   | n | Wk 0 | Wk 1(S) | Wk 4(S) | Wk 12(S) | Wk 26(S) | WK 52(S) |
|---|---|------|---------|---------|----------|----------|----------|
| I  | 35 | 100 | 34.3 | 22.9 | 20.0 | 16.7 | 13.3 |
| II | 35 | 100 | 91.4 | 85.5 | 82.5 | 78.9 | 78.9 |

|   | Wk 0 | Wk 1(F) | Wk 4(f) | Wk 12(F) | Wk 26(F) | Wk 52(F) |
|---|------|---------|---------|----------|----------|----------|
| I  | 35 | 100 | 65.7 | 77.1 | 80.0 | 83.3 | 86.7 |
| II | 35 | 100 | 08.6 | 14.5 | 17.5 | 21.1 | 21.1 |

$p<0.001$ from 2×2 Chi-square statistical test and Mantel-Cox statistical test.

Summary: Of the patients in control group I, 85.7% failed to stop smoking within the test period; in experimental group II, 20.0% failed to stop smoking within the test period, a highly significant statistical difference.

EXAMPLE II

A. Baseline Comparability

The groups were comparable at baseline except for packs of cigarettes ("packs") smoked per day. Statistical testing was done by one-way analysis of variance for continuous variables and chi-square test for categorical variables. P-value for one-way analysis of variance was $p=0.003$. Multiple comparisons of the three means indicate that Group 2>PLBO ($p<0.01$) and Group 1>PLBO ($p.<0.10$).

|   | Group 1 N = 35 | Group 2 N = 35 | PLBO N = 35 |
|---|---|---|---|
| male, n (%) | 23 (65.7) | 18 (51.4) | 20 (57.1) |
| age, mean | 40.0 | 37.2 | 36.8 |
| packs smoked per day, mean | 2.6 | 2.8 | 1.8 |
| smoking satiation, mean | 3.0 | 3.3 | 2.7 |

B. Smoking Satiation After Treatment

Values range from 0=no satiation to 10=maximum satiation measured at five time points.

The following analysis by repeated measures analysis of variance only used patient data where values were available at all time points.

| Mean Smoking Satiation Score | | | | | | |
|---|---|---|---|---|---|---|
|   | n | Wk 1 | Wk 4 | Wk 12 | Wk 26 | Wk 52 | Overall |
| Group 1 | 23 | 4.3 | 3.8 | 3.6 | 3.4 | 3.4 | 3.7 |
| Group 2 | 25 | 8.4 | 8.0 | 7.6 | 7.7 | 7.4 | 7.8 |
| PLBO | 25 | 2.9 | 3.0 | 3.0 | 3.0 | 3.2 | 3.0 | treatment effect $p < .001$
time effect $p = .026$
treatment*time interaction $p = .084$ In the following analysis, missing values were estimated for patients who were missing values at one or two time points, as a result of the failure of the patient to appear at the weekly evaluation session, and the values were analyzed as above further including these patients. The estimate used was the last available value for that patient. Since there was not much variation in time after Wk 4, this approach was deemed statistically reliable. In this analysis, patients missing 3 or more data points were excluded.

|   | n | Wk 1 | Wk 4 | Wk 12 | Wk 26 | Wk 52 | Overall |
|---|---|---|---|---|---|---|---|
| Group 1 | 30 | 4.2 | 3.7 | 3.5 | 3.4 | 3.4 | 3.6 |
| Group 2 | 33 | 8.7 | 8.2 | 7.6 | 7.7 | 7.4 | 7.9 |
| PLBO | 29 | 3.0 | 2.9 | 3.0 | 3.0 | 3.2 | 3.0 | treatment effect $p < .001$
time effect $p < .001$
treatment*time interaction $p < .01$ An alternate analysis of this data comprises multiple comparisons at each time point using all available data at each time point. The mean values changed only slightly, and the conclusions were the same.

|   | Wk 1 | | Wk 4 | | Wk 12 | | Wk 26 | | Wk 52 | |
|---|---|---|---|---|---|---|---|---|---|---|
|   | n | mean | n | mean | n | mean | n | mean | n | mean |
| Group 1 | 35 | 4.2 | 33 | 3.5 | 30 | 3.5 | 26 | 3.6 | 23 | 3.4 |
| Group 2 | 35 | 8.7 | 33 | 8.2 | 33 | 7.6 | 29 | 7.6 | 26 | 7.1 |
| PBLO | 35 | 3.0 | 32 | 2.8 | 29 | 3.0 | 25 | 3.0 | 26 | 3.2 |
| p-value | <.001 | | <.001 | | <.001 | | <.001 | | <.001 | |
| GRP2 > GRP1 | <.001 | | <.001 | | <.001 | | <.001 | | <.001 | |
| GRP2 > PLBO | <.001 | | <.001 | | <.001 | | <.001 | | <.001 | |
| GRP1 > PLBO | <.05 | | NS | | NS | | NS | | NS | |
| Conclusion: | Group 2 > Group 1 at all time points Group 2 > PLBO at all time points No difference between Group 1 and PLBO PLBO group: no change over time | | | | | | | | | |

C. Smoking Status

1. This status comprises variables coded Success (meaning stopped smoking) and Failure (meaning failure to stop smoking) describing each patient's status at each time point recorded. In all cases S never follows F. That is, a patient fails and remains in that category; it is not a variable that is independently measured at each visit. Once a value of F is recorded, the patient remains in that category; the variable is thus not appropriate for repeat measure analysis of variance. Therefore, one variable was defined to describe smoking status.

Success = all values are S
Failure = at least one value is F

The time to the first failure was also calculated for use in Kaplan-Meier life table analysis (below).

The analysis performed multiple comparison tests using data available at each time point separately.

| | % fail to stop | | |
|---|---|---|---|
| | den | num | % |
| Group 1 | 35 | 30 | 85.7 |
| Group 2 | 35 | 7 | 20.0 |
| PLBO | 35 | 32 | 91.4 | p < .001 from 2 × 3 Chi-square test

2. Life Table Analysis:

| | Cumulative rate of success for stop smoking | | | | | |
|---|---|---|---|---|---|---|
| | Wk 0 | Wk 1 | Wk 4 | Wk 12 | Wk 26 | Wk 52 |
| Group 1 | 100. | 34.3 | 22.9 | 20.0 | 16.7 | 13.3 |
| Group 2 | 100. | 91.4 | 85.5 | 82.5 | 78.9 | 78.9 |
| PLBO | 100. | 20.0 | 10.0 | 10.0 | 10.0 | 5.0 | p < .001 for comparison of the curves using Mantel-Cox statistic

The life-table analysis also gave similar results, % fail in Group 1 > Group 2 (or % success Group 2 > Group 1) and % fail in PLBO > Group 2 (or % success Group 2 > PLBO). There was no difference between Group 1 and PLBO.

The FIGURE is a graphical presentation of the data, illustrating the total number of patients in each group reporting complete abstinence from smoking from the beginning of the study to each data (time) point, on a percentage basis (Cumulative Proportion Successful).

What is claimed is:

1. A method for alleviating symptoms of nicotine withdrawal in a human habituated to tobacco who has curtailed the use of tobacco comprising orally administering to the human for at least about 4 weeks an alkalizing composition consisting essentially of calcium carbonate in an amount sufficient to neutralize or alkalize the urine to alleviate said symptoms.

2. The method of claim 1, wherein the calcium carbonate is administered in an oral dosage sufficient to maintain the pH of the urine for at least about 7 weeks.

3. The method of claim 2, wherein the oral dosage is administered at least once per day.

4. The method of claim 2, wherein the oral dosage comprises from about 2 to 10 grams calcium carbonate per day.

5. The method of claim 4, wherein the dosage is administered at least twice daily in about equal amounts.

6. The method of claim 1, wherein the calcium carbonate composition is administered for at least about four consecutive weeks.

7. The method of claim 1, wherein the oral dosage comprises from about 6 to 10 grams of calcium carbonate administered at least once per day for one week, and thereafter from about 2 to 6 grams calcium carbonate per day until withdrawal symptoms are alleviated.

8. The method of claim 7, wherein the calcium carbonate composition is administered for at least about 4 weeks.

9. The method of claim 1, wherein an alkalinizing composition consisting essentially of calcium carbonate and karaya gum is administered to the human.

10. The method of claim 9, wherein the karaya gum and calcium carbonate are administered in a ratio of about 18 parts carbonate to about one part gum.

11. The method of claim 10, wherein the administration of carbonate and gum is combined with a restricted calorie diet and exercise to release an amount of beta-endorphins at least sufficient to sustain habituation levels of beta-endorphins.

12. A method for dehabituating a human to the use of tobacco, comprising orally administering to the human for at least about 4 weeks an alkalizing composition consisting essentially of calcium carbonate in an amount sufficient to neutralize or alkalize the urine.

13. The method of claim 12, wherein the calcium carbonate is administered in an oral dosage sufficient to maintain the pH of the urine for at least about 7 weeks.

14. The method of claim 13, wherein the oral dosage is administered at least once per day.

15. The method of claim 13, wherein the oral dosage comprises from about 2 to 10 grams calcium carbonate per day.

16. The method of claim 15, wherein the dosage is administered at least twice daily in about equal amounts.

17. The method of claim 12, wherein the human is administered to for at least about four weeks.

18. The method of claim 13, wherein the oral dosage comprises from about 6 to 10 grams of calcium carbonate administered at least once per day for at least one weeks, and from about 2 to 6 grams calcium carbonate per day for at least three additional weeks.

19. The method of claim 18, wherein the calcium carbonate is administered for about four weeks.

20. The method of claim 12, wherein the calcium carbonate is administered in combination with karaya gum.

21. The method of claim 20, wherein the karaya gum and calcium carbonate are administered in a ratio of about 18 parts carbonate to about one part gum.

22. The method of claim 22, wherein the carbonate and gum are administered as a drink comprising carbonate and gum dissolved in a liquid.

23. The method of claim 22, further comprising a restricted calorie diet and exercise sufficient to release an amount of beta-endorphins of at least about habituation levels.

* * * * *